US009610232B2

(12) United States Patent
Farwick et al.

(10) Patent No.: US 9,610,232 B2
(45) Date of Patent: *Apr. 4, 2017

(54) USE OF SPHINGANINE TO IMPROVE THE VISUAL APPEARANCE OF SKIN AND HAIR

(75) Inventors: Mike Farwick, Essen (DE); Tim Koehler, Dorsten (DE); Matthias Mentel, Dortmund (DE)

(73) Assignee: EVONIK DEGUSSA GMBH, Essen (DE)

( * ) Notice: Subject to any disclaimer, the term of this patent is extended or adjusted under 35 U.S.C. 154(b) by 40 days.

This patent is subject to a terminal disclaimer.

(21) Appl. No.: 14/236,696

(22) PCT Filed: Jul. 4, 2012

(86) PCT No.: PCT/EP2012/062966
§ 371 (c)(1),
(2), (4) Date: Feb. 3, 2014

(87) PCT Pub. No.: WO2013/017361
PCT Pub. Date: Feb. 7, 2013

(65) Prior Publication Data
US 2014/0170092 A1    Jun. 19, 2014

(30) Foreign Application Priority Data
Aug. 3, 2011 (DE) .................. 10 2011 109 546

(51) Int. Cl.
| *A61K 8/41* | (2006.01) |
| *A61K 8/34* | (2006.01) |
| *A61Q 19/00* | (2006.01) |
| *A61Q 5/00* | (2006.01) |
| *A61Q 5/02* | (2006.01) |
| *A61Q 5/12* | (2006.01) |
| *A61Q 15/00* | (2006.01) |
| *A61Q 11/00* | (2006.01) |
| *A61Q 17/04* | (2006.01) |
| *A61Q 19/10* | (2006.01) |

(52) U.S. Cl.
CPC .................. *A61K 8/41* (2013.01); *A61Q 5/00* (2013.01); *A61Q 5/002* (2013.01); *A61Q 5/006* (2013.01); *A61Q 5/02* (2013.01); *A61Q 5/12* (2013.01); *A61Q 15/00* (2013.01); *A61Q 19/00* (2013.01); *A61Q 19/008* (2013.01); *A61Q 11/00* (2013.01); *A61Q 17/04* (2013.01); *A61Q 19/10* (2013.01)

(58) Field of Classification Search
None
See application file for complete search history.

(56) References Cited

U.S. PATENT DOCUMENTS

| 5,514,672 | A * | 5/1996 | Bazzano | A61K 8/4953 424/70.1 |
| 5,882,665 | A | 3/1999 | Meyers et al. | |
| 6,696,069 | B2 | 2/2004 | Harichian et al. | |
| 2004/0170591 | A1 * | 9/2004 | Allart | A61K 31/133 424/70.21 |
| 2007/0238764 | A1 * | 10/2007 | Allart | A61K 8/675 514/356 |
| 2010/0184733 | A1 | 7/2010 | Korevaar et al. | |

FOREIGN PATENT DOCUMENTS

| CH | 399 655 A | 9/1965 | |
| CN | 1374078 A | 10/2002 | |
| CN | 1747710 A | 3/2006 | |
| CN | 101083973 A | 12/2007 | |
| EP | 1 287 815 A1 | 3/2003 | |
| FR | WO 02060406 A2 * | 8/2002 | ............... A61K 8/68 |
| JP | 585924 A | 4/1993 | |
| JP | 8-508742 A | 9/1996 | |
| JP | 2004501951 A | 1/2004 | |
| WO | 94/23694 A1 | 10/1994 | |
| WO | 02/02072 A2 | 1/2002 | |
| WO | 02/060406 A2 | 8/2002 | |
| WO | WO 2008/043386 A1 * | 4/2008 | ............... A61K 8/68 |

OTHER PUBLICATIONS

Youn et al., British Journal of Dermatology, 2005, 153, 919-924.*
Mintel, XP-002687701 "Voluminising Detangler" (Oct. 2010), Database GNPD Accession No. 1418736, 2 pages.
Mintel, XP-002687702 "Intensive Repair Masque" (Feb. 2010), Database GNPD Accession No. 1272283, 2 pages.
Thomson Scientific, XP-002687703 (Sep. 16, 1997), Week 199747.
International Search Report dated Dec. 19, 2012 issued in PCT/EP2012/062966.
Japanese Office Action dated Mar. 8, 2016, received in a corresponding foreign application with an English-language translation thereof.
Chinese Office Action dated Apr. 30, 2015 from related Chinese Patent Application No. 201280038494.1.
Japanese Office Action dated Oct. 19, 2016 received in a corresponding foreign application with an English-language translation thereof.

\* cited by examiner

*Primary Examiner* — Abigail Fisher
(74) *Attorney, Agent, or Firm* — Scully, Scott, Murphy & Presser, P.C.

(57) ABSTRACT

The invention relates to the use of sphinganine for improving the visual appearance of skin and hair, for caring for, for protecting and/or for stimulating the growth of skin and hair.

8 Claims, 1 Drawing Sheet

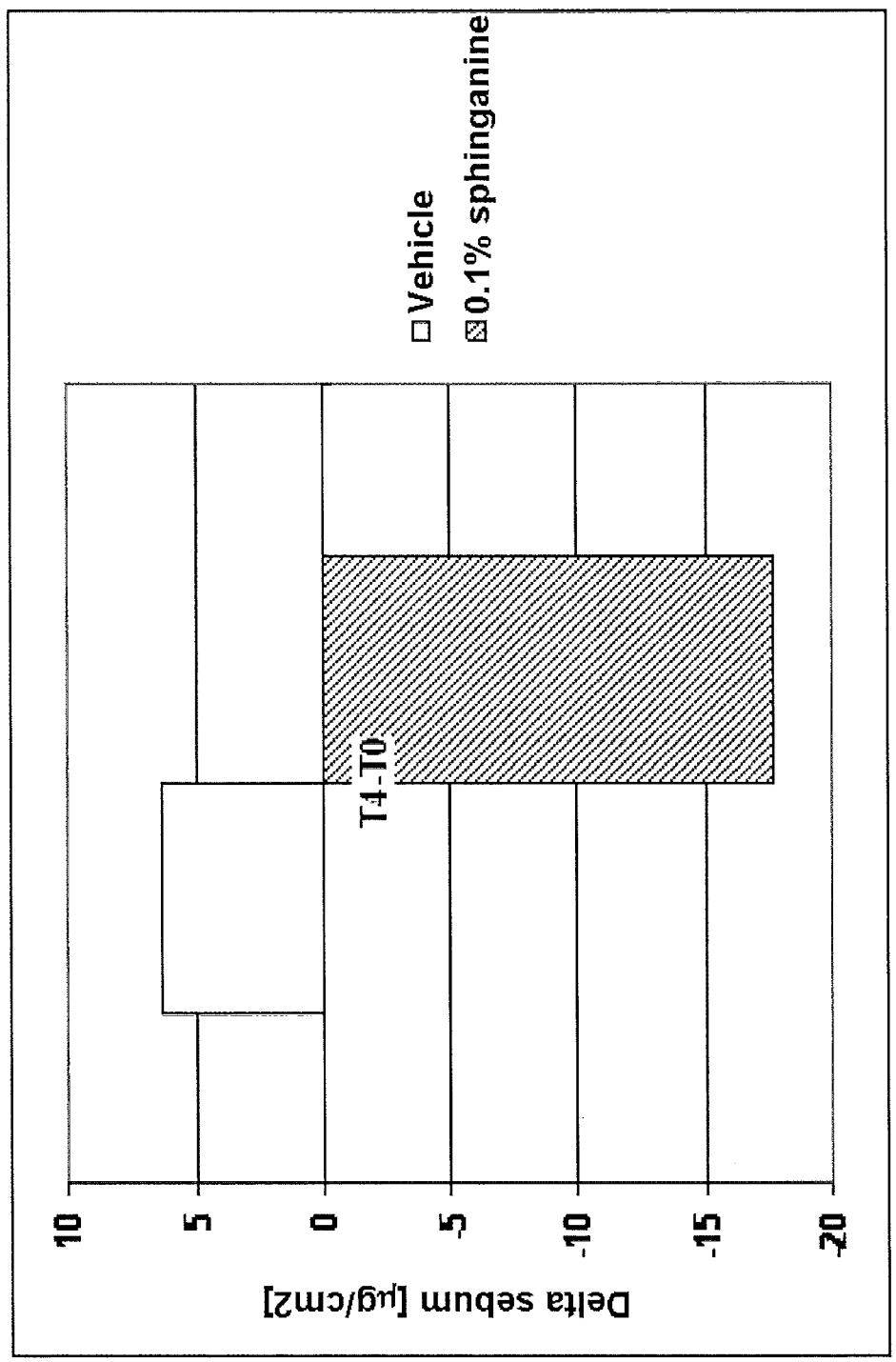

USE OF SPHINGANINE TO IMPROVE THE VISUAL APPEARANCE OF SKIN AND HAIR

FIELD OF THE INVENTION

The invention relates to the use of sphinganine for improving the visual appearance of skin and hair, for caring for, for protecting and/or for stimulating the growth of skin and hair.

PRIOR ART

Ceramides and their use in cosmetic products for caring for skin and/or hair have been known for a long time.

Their preparation is complex.

It was an object of the invention to provide compounds that care for the skin and/or the skin appendages and have a similar activity spectrum to ceramides but can be prepared more easily.

DESCRIPTION OF THE INVENTION

Surprisingly, it has been found that sphinganine, a precursor of the ceramides, is able to achieve this object.

The present invention therefore provides the use of sphinganine for caring for, for protecting and/or for stimulating the growth of skin, nails and hair. In this connection, it may be mentioned that hair also encompasses fur of animals.

According to the invention, sphinganine is used as a cosmetic active ingredient for caring for the skin, it being possible to care for a very wide variety of skin types, e.g. normal skin, young skin, chronologically aged skin, photoaged skin.

Here, sphinganine is used in such a way that it strengthens the epidermal lipid barrier. The care effect can primarily be explained by a strengthening as a result of absorption and incorporation of the sphinganine into corresponding barrier lipids.

Consequently, sphinganine leads to the repair of the damaged lipid barrier.

According to the invention, sphinganine is used for repairing the damaged lipid barrier. Sphinganine likewise has a protective effect against harmful intrinsic and extrinsic influential factors. Consequently, sphinganine is used according to the invention for preventing damage to cellular macromolecules and to the epidermal lipid barrier.

Sphinganine is used according to the invention to promote the differentiation of epidermal keratinocytes. This has a positive influence on the formation of the epidermal skin barrier.

Sphinganine is additionally used according to the invention to switch on the modulation of the gene expression the biosynthesis of epidermal barrier lipids.

A further subject matter of the present invention is the use of sphinganine for inhibiting ceramidases; this advantageously suppresses the degradation of barrier ceramides.

The cosmetic use of sphinganine leads in general to an improvement in skin structure, especially of aged skin, as a result of which sphinganine is used according to the invention as a universal antiaging active ingredient.

Sphinganine also shows a positive effect in the sense of a reduction in the pore size of the skin, as a result of which the appearance of the skin overall is improved.

Consequently, further subjects of the present invention are the cosmetic use of sphinganine for improving the skin appearance and the cosmetic use of sphinganine for reducing the pore size of the skin.

Gene expression studies in cell cultures showed that sphinganine beneficially modulated the expression of so-called stem cell markers, as a result of which an antiaging effect can be achieved. A further subject matter of the present invention is consequently the cosmetic use of sphinganine for modulating stem cell markers.

Sphinganine is additionally used cosmetically according to the invention for reducing skin roughness.

Sphinganine is additionally used cosmetically according to the invention for reducing skin flakiness.

Sphinganine is additionally used cosmetically according to the invention for reducing the depth of wrinkles in the skin.

Sphinganine is additionally used cosmetically according to the invention for strengthening the skin elasticity.

Sphinganine is additionally used cosmetically according to the invention for increasing the tautness of the skin.

Sphinganine is additionally used cosmetically according to the invention for increasing the thickness of the skin.

Sphinganine is additionally used cosmetically according to the invention for reducing an increased transepidermal water loss of the skin.

Sphinganine is additionally used cosmetically according to the invention for increasing skin moisture.

Sphinganine is used according to the invention for protecting the skin, particularly skin which has a diminished epidermal barrier function as a result of certain skin diseases; however, in principle, all types of skin can be protected against adverse environmental influences by using sphinganine.

A further subject matter of the present invention is sphinganine for treating xerosis.

A further subject matter of the present invention is sphinganine for treating atopic dermatitis.

A further subject matter of the present invention is sphinganine for treating contact dermatitis.

A further subject matter of the present invention is sphinganine for treating psoriasis.

A further subject matter of the present invention is sphinganine for treating ichthyosis.

A further subject matter of the present invention is sphinganine for treating acanthosis.

A further subject matter of the present invention is sphinganine for treating dandruff.

A further subject matter of the present invention is sphinganine for treating photodermatitis.

A further subject matter of the present invention is sphinganine for treating erythema.

A further subject matter of the present invention is sphinganine for treating keratinizing disorders.

A further subject matter of the present invention is sphinganine for treating hornification defects.

A further subject matter of the present invention is sphinganine for treating vascular diseases.

A further subject matter of the present invention is sphinganine for treating cellulite.

Sphinganine has an antimicrobial effect. A further subject matter of the present invention is sphinganine for treating infectious diseases of the skin.

A further subject matter of the present invention is sphinganine for normalizing skin flora.

A further subject matter of the present invention is sphinganine for inhibiting the growth of pathogenic skin germs, in particular bacteria and fungi selected from *Malessezia furfur, Staphylococcus epidermidis, Candida albicans, Staphylococcus aureus, Corynebacterium xerosis, Micrococcus luteus, Propionibacterium acnes, Escherichia coli,*

*Pseudomonas aeruginosa, Microsporum canis, Streptococcus pyogenes, Brevibacterium epidermidis.*

On account of its antimicrobial effect, sphinganine is also used cosmetically according to the invention as a deodorant or antiperspirant active ingredient. The antimicrobial effect leads to a reduction in skin germs which are the cause of the bad odours as a result of perspiration. Consequently, sphinganine is used according to the invention for reducing the odour formation as a result of perspiration.

On account of its antimicrobial effect, sphinganine can also be used very well for oral dental care products in order to restrict the growth of caries-causing germs in mouth flora. Analogously, sphinganine can also be used in corresponding formulations with antimicrobial effects for further mucosa (eye and nose mucosa etc.).

The antimicrobial properties of sphinganine also permit a use as natural preservative, both for cosmetic and for non-cosmetic applications.

The topical application of sphinganine on the skin leads to a reduction in inflammatory reactions, as a result of which skin irritation is counteracted and the skin is calmed.

Consequently, sphinganine is suitable to a particular extent for cosmetic products for calming irritated skin.

A further subject matter of the present invention is sphinganine for treating inflammatory diseases of the skin.

A further subject matter of the present invention is sphinganine for treating acne.

A skin-calming effect of sphinganine is also observed on reddened skin which has been caused in particular as a consequence of solar irradiation, sunburn and/or skin reddening (erythema). In this regard, sphinganine is also used as an active ingredient for sun protection and aftersun products.

The anti-inflammatory and skin-calming effect of sphinganine leads to an advantageous use according to the invention of sphinganine in skin-calming aftershave lotions.

Sphinganine is likewise used cosmetically on skin in order to alleviate certain effects such as dry, itchy and flaky skin which arise as a consequence of autoimmune diseases (e.g. psoriasis).

A further use option of sphinganine relates to the disorder of the skin desquamation processes. Thus, sphinganine leads to a normalization of the natural keratinocyte proliferation and desquamation processes in the skin, as a result of which corresponding disturbances A further subject matter of the present invention is sphinganine for treating disorders of skin desquamation processes.

A further use according to the invention of sphinganine relates to the modulation of skin tone. For example, sphinganine, presumably on account of its gene-regulatory effect, has the potential to influence skin coloration either positively (tanning effect) or negatively (skin lightening). Consequently, sphinganine can be used simultaneously as a skin lightener or as a skin tanning agent. Similarly, sphinganine can be used for normalizing the skin tone in cases of pigment disorders (inter alia liver spots, moles, freckles, melasma, age spots).

A further subject matter of the present invention is consequently the cosmetic use of sphinganine for normalizing the skin tone. A further subject matter of the present invention is sphinganine for treating pigmentation disorders.

A use of sphinganine in the form of special eye care products leads to a reduction in the extent of dark rings under the eyes, brought about by an improvement in vascular supply, circulation and nutrient supply of the corresponding tissue (microcirculation). A further subject matter of the present invention is the cosmetic use of sphinganine for reducing dark circles around the eyes.

In the form of special lip care products, sphinganine can advantageously be used cosmetically for outlining the lip tissue.

Sphinganine can be used particularly advantageously for stimulating hair growth on the scalp. Besides the stimulation of hair growth, sphinganine also has a promoting effect on the structure of the hair, as a result of which its stability, strength, colour intensity and load-bearing capacity is increased.

A further subject matter of the present invention is sphinganine for treating hair loss.

A further subject matter of the present invention is the use of sphinganine for conditioning hair.

Sphinganine is used advantageously in cosmetics; in this connection, the use of sphinganine is not limited to leave-on applications. Sphinganine can also advantageously be used in the form of rinse-off applications (e.g. shampoos, skin cleansers) and leave-in applications (e.g. hair conditioners).

In particular, sphinganine is used cosmetically according to the invention as an active ingredient to combat oily skin. A further subject matter of the present invention is sphinganine for reducing the production of grease or sebum in the skin, in particular human skin.

This in turn leads to an improvement in the visual appearance of the skin, in particular human skin, as a result of which sphinganine is used cosmetically according to the invention in order to improve the visual appearance of the skin by reducing skin shine.

Used on the scalp in particular, a cosmetic use according to the invention of sphinganine leads to an improvement in the visual appearance of the hair, in particular human hair, by reducing the production of sebum and therefore of sebum sticking to the hair.

The examples listed below describe the present invention by way of example without any intention of limiting the invention, the scope of application of which arises from the entire description and the claims, to the embodiments specified in the examples.

Unless stated otherwise, all of the stated percentages (%) are percentages by mass.

The following FIGURES form part of the examples:

FIG. 1:

EXAMPLES

Example 1

Reduction in Sebum Production as a Result of Sphinganine

In order to demonstrate the reduction in sebum production of the skin by topical application of sphinganine, a human sebum study was carried out.

The panel comprised 30 female subjects aged 21-45 years, with 14 subjects applying a lotion containing 0.1% sphinganine and 16 subjects applying a lotion without sphinganine (vehicle control). The composition of the formulation is shown in the following table:

TABLE 1

Test formulations. Data in percent by mass.

| Raw material | INCI | Sphinganine formulation | Vehicle formulation |
|---|---|---|---|
| TEGINACID ® C | Ceteareth-25 | 2.0 | 2.0 |
| ABIL ® Care 85 | Bis-PEG/PPG-16/16 PEG/PPG16/16 Dimethicone; Caprylic/Capric Triglyceride | 1.0 | 1.0 |
| TEGO ® Alkanol 18 | Stearyl Alcohol | 3.5 | 3.5 |
| TEGOSOFT ® G20 | Octyl Dodecanol | 5.0 | 5.0 |
| TEGOSOFT ® APM | PPG-13 Myristyl Ether | 3.0 | 3.0 |
| TEGOSOFT ® DEC | Diethylhexyl Carbonate | 2.0 | 2.0 |
| Sphinganine | Sphinganine | 0.1 | — |
| Water | Water | 82.68 | 82.78 |
| Lactic acid (10%) | Lactic Acid | 0.5 | 0.5 |
| Euxyl K220 | Methylisothiazolinone, Ethylhexylglycerin, Water | 0.12 | 0.12 |
| Perfume | | 0.1 | 0.1 |

To prepare the formulations, customary formulation processes known to the person skilled in the art were used.

The application phase comprised 28 days, with application taking place twice daily (morning and evening) to the forehead.

The skin sebum was measured using a Sebumeter SM 815® from Courage+Khazaka electronic GmbH, Cologne, Germany. The measurements were taken in the middle of the forehead in the region of the glabella lines. The average value calculated from the individual values of three repeat measurements was registered. On the evening before each measurement no formulation was applied. Three hours before the measurement, the forehead was cleaned using a wipe (babylove sensitive wipes, dm-drogerie markt, Karlsruhe, Germany). The measurements were carried out in each case at a time of day defined individually for each subject in the period between 12:00 and 14:30 hours. The sebum value at time point T0 before the application phase and T4 after 28 days was determined.

As the human in vivo study showed, over the period of 28 days, a slight, but not statistically significant increase in sebum production could be observed in the group of people who applied the vehicle formulation.

In the group of people who applied 0.1% sphinganine, a statistically significant reduction in sebum production was registered compared to the starting value and also compared to the vehicle group.

These results show that a significant reduction in sebum production can be achieved on account of using sphinganine.

Example 2

Reduction in Hair Grease Production as a Result of Sphinganine

In order to demonstrate the reduction in hair grease production as a result of treating the scalp with sphinganine, a human study was carried out as to the health of the scalp. The panel comprised 32 subjects (mixed male/female, minimum age 30, with a tendency for greasy scalp/greasy hair), with 16 subjects in each case applying a hair tonic with 0.2% sphinganine or without sphinganine (vehicle control).

The composition of the hair tonic is shown in the following table:

TABLE 1

Test hair tonic. Data in percent by mass

| Raw material | INCI | Sphinganine hair tonic | Vehicle hair tonic |
|---|---|---|---|
| Teginacid C | Ceteareth-25 | 3 | 3 |
| Sphinganine | Sphinganine | 0.2 | — |
| Ethanol | Ethanol | 50 | 50 |
| Water | Water | 46.7 | 46.9 |
| Lactic acid (10%) | Lactic Acid | ad pH 5.5 | ad pH 5.5 |
| Perfume | | 0.1 | 0.1 |

To prepare the hair tonic, customary formulation processes known to the person skilled in the art were used.

The application phase comprised 4 months, with the hair tonic being applied to the scalp twice daily (morning and evening) with the help of a pipette with a defined volume of 3 mL, and gently massaged in using the hands. The test parameters included the shine of the hair and the greasiness of the scalp.

The greasiness of the scalp is carried out firstly by means of a subjective evaluation (self and expert estimation), and secondly by means of a "Sebutape" method in accordance with manufacturers instructions.

Time points for carrying out the measurements were before the start of application, after two months and after four months.

The results showed that a significant reduction in hair grease production can be achieved on account of using sphinganine.

Example 3

Example Formulations

Example Formulation 3.1

Skin-Tightening O/W Sunscreen Lotion

| | |
|---|---|
| Glyceryl Stearate Citrate | 2.00% |
| Cetearyl Alcohol | 1.00% |
| C12-15 Alkyl Benzoate | 5.00% |
| Triisostearin | 1.00% |
| Diethylhexyl Carbonate | 4.00% |
| Octocrylene | 6.00% |
| Bis-Ethylhexyloxyphenol Methoxyphenyl Triazine | 2.00% |
| Ethylhexyl Salicylate | 4.00% |
| Caprylic/Capric Triglyceride; Xymenynic Acid | 1.50% |
| Xanthan Gum | 0.20% |
| Sphinganine | 1.00% |
| Titanium Dioxide; Trimethoxycaprylylsilane; Glycerin | 3.00% |
| Glycerin | 3.00% |
| Water | ad 100.00% |
| Paraffinum Perliquidum | 0.80% |
| Carbomer | 0.20% |
| Sodium Hydroxide (10% in water) | 0.65% |

Example Formulation 3.2

Leave-In Conditioner

| | |
|---|---|
| Hydrolyzed Keratin | 2.50% |
| Water | ad 100.00% |
| Sodium Lactate; Sodium PCA; Glycine; Fructose; Urea; Niacinamide; Inositol; Sodium Benzoate; Lactic Acid | 2.00% |
| PEG-40 Hydrogenated Castor Oil | 1.00% |
| Quaternium-80 | 1.50% |
| Ethanol | 15.00% |
| PVP/VA Copolymer | 4.00% |
| Sphinganine | 0.10% |
| Cocamidopropyl Betaine | 4.00% |
| Citric Acid (30%) | 3.00% |

Example Formulation 3.3

Leave-In Conditioning Spray

| | |
|---|---|
| Laureth-4 | 0.5% |
| PEG-40 Hydrogenated Castor Oil | 0.5% |
| Sphinganine | 0.1% |
| Quaternium-80 | 0.4% |
| Dimethicone Propyl PG-Betaine | 0.6% |
| Cetrimonium Chloride | 0.8% |
| Water | ad 100.0% |
| Creatine | 0.5% |
| Ethanol | 15.0% |
| PVPNA Copolymer | 4.0% |
| Sodium Hydroxide (10% in water) | 1.2% |

Example Formulation 3.4

O/W Lotion

| Formulation | 3.4.1 | 3.4.2 | 3.4.3 | 3.4.4 | 3.4.5 | 3.4.6 |
|---|---|---|---|---|---|---|
| Decyl Oleate | 5.7% | 5.7% | 5.7% | 5.7% | 5.7% | 5.7% |
| Ethylhexyl Stearate | 7.3% | 7.3% | 7.3% | 7.3% | 7.3% | 7.3% |
| Glyceryl Stearate | 0.5% | 0.5% | 0.5% | 0.5% | 0.5% | 0.5% |
| Stearic Acid | 0.7% | 0.7% | 0.7% | 0.7% | 0.7% | 0.7% |
| Ceteareth-25; Glycerin; Cetyl Alcohol; Behenic Acid; Cholesterol; Ceramide EOP; Ceramide EOS; Ceramide NP; Ceramide NS; Ceramide AP; Caprooyl-Phytosphingosine; Caproyl-Sphingosine. | — | 1.0% | — | 0.5% | — | 0.5% |
| Salicyloyl Phytosphingosine | — | — | 0.1% | — | 0.05% | 0.03% |
| Creatine | 0.5% | — | — | 0.2% | 0.1% | 0.2% |
| Cetearyl Glucoside | 1.0% | 1.0% | 1.0% | 1.0% | 1.0% | 1.0% |
| Glycerin | 3.0% | 3.0% | 3.0% | 3.0% | 3.0% | 3.0% |
| Carbomer | 0.2% | 0.2% | 0.2% | 0.2% | 0.2% | 0.2% |
| Sodium Hydroxide (10%) | 0.7% | 0.7% | 0.7% | 0.7% | 0.7% | 0.7% |
| Ethanol | 9.5% | 9.5% | 4.75% | 5.7% | 3.8% | 7.6% |
| Sphinganine | 0.33% | 0.33% | 0.16% | 0.20% | 0.13% | 0.26% |
| Water | ad 100.0% | ad 100.0% | ad 100.0% | ad 100.0% | ad 100.0% | ad 100.0% |

Example Formulation 3.5

O/W Cream

| Formulation | 3.5.1 | 3.5.2 | 3.5.3 | 3.5.4 | 3.5.5 | 3.5.6 |
|---|---|---|---|---|---|---|
| Glyceryl Stearate | 2.5% | 2.5% | 2.5% | 2.5% | 2.5% | 2.5% |
| Stearic Acid | 1.0% | 1.0% | 1.0% | 1.0% | 1.0% | 1.0% |
| Stearyl Alcohol | 1.5% | 1.5% | 1.5% | 1.5% | 1.5% | 1.5% |
| Decyl Cocoate | 8.0% | 8.0% | 8.0% | 8.0% | 8.0% | 8.0% |
| Ethylhexyl Stearate | 7.8% | 7.8% | 7.8% | 7.8% | 7.8% | 7.8% |
| Caprylic/Capric Triglyceride | 5.0% | 5.0% | 5.0% | 5.0% | 5.0% | 5.0% |
| Salicyloyl Phytosphingosine | — | — | 0.05% | — | 0.1% | 0.05% |
| Ceramide 3 | — | — | — | 0.05% | — | 0.05% |
| Cetearyl Glucoside | 1.0% | 1.0% | 1.0% | 1.0% | 1.0% | 1.0% |
| Glycerin | 3.0% | 3.0% | 3.0% | 3.0% | 3.0% | 3.0% |
| Carbomer | 0.2% | 0.2% | 0.2% | 0.2% | 0.2% | 0.2% |
| Sodium Hydroxide (10%) | 0.7% | 0.7% | 0.7% | 0.7% | 0.7% | 0.7% |
| Polyglutamic Acid; Hydrolised Sclerotium Glucan; Betaine; Urea; | 5.0% | 5.0% | 5.0% | 5.0% | 5.0% | 5.0% |

-continued

| Formulation | 3.5.1 | 3.5.2 | 3.5.3 | 3.5.4 | 3.5.5 | 3.5.6 |
|---|---|---|---|---|---|---|
| Potassium Lactate | | | | | | |
| Hyaluronic Acid | — | 0.05% | — | — | 0.05% | 0.1% |
| Ethanol | 1.9% | 3.8% | 4.75% | 4.75% | 1.9% | 2.85% |
| Sphinganine | 0.07% | 0.13% | 0.16% | 0.16% | 0.07% | 0.10% |
| Water | ad 100.0% | ad 100.0% | ad 100.0% | ad 100.0% | ad 100.0% | ad 100.0% |

Example Formulation 3.6

W/O Lotion

| Formulation | 3.6.1 | 3.6.2 | 3.6.3 | 3.6.4 | 3.6.5 |
|---|---|---|---|---|---|
| Cetyl PEG/PPG-10/1 Dimethicone | 2.0% | 2.0% | 2.0% | 2.0% | 2.0% |
| Microcristalline Wax | 0.5% | 0.5% | 0.5% | 0.5% | 0.5% |
| Hydrogenated Castor Oil | 0.5% | 0.5% | 0.5% | 0.5% | 0.5% |
| Decyl Oleate | 9.0% | 9.0% | 9.0% | 9.0% | 9.0% |
| Caprylic/Capric Triglyceride | 10.0% | 10.0% | 10.0% | 10.0% | 10.0% |
| Diethylhexyl Carbonate | 5.0% | 5.0% | 5.0% | 5.0% | 5.0% |
| PPG-3 Myristyl Ether; Salicyloyl Phytosphingosine | 3.0% | 3.0% | 3.0% | 3.0% | 3.0% |
| Sodium Chloride | 0.5% | 0.5% | 0.5% | 0.5% | 0.5% |
| Creatine | — | 0.2% | — | — | 0.1% |
| Betaine | — | — | 0.3% | — | 0.3% |
| Urea | — | — | — | 0.5% | 0.1% |
| Ethanol | 3.8% | 1.9% | 4.75% | 1.9% | 2.85% |
| Sphinganine | 0.13% | 0.07% | 0.16% | 0.07% | 0.1% |
| Water | ad 100.0% | ad 100.0% | ad 100.0% | ad 100.0% | ad 100.0% |

Example Formulation 3.7

Massage Oil

| | |
|---|---|
| Stearyl alcohol | 2.0% |
| Petrolatum | 4.0% |
| Dimethicone | 2.0% |
| Isopropyl palmitate | 6.0% |
| Cetylstearyl alcohol | 4.0% |
| PEG-40 hydrogenated castor oil | 2.0% |
| Sphinganine | 0.2% |
| Glycerin | 3.0% |
| Water | ad 100 |

Example Formulation 3.8

Shower Gel

| | |
|---|---|
| PEG-7 Glyceryl Cocoate | 2.0% |
| PEG-40 Hydrogenated Castor Oil | 2.5% |
| Sucrose Cocoate | 2.5% |
| Perfume | 0.5% |
| Water | ad 100% |
| Sphinganine | 0.2% |
| Cocamidopropyl Betaine | 10.5% |
| Sodium Lactate, Sodium PCA Glycine, Fructose, Urea, Niacinamide, Inositol, Sodium benzoate, Lactic Acid, | 1.0% |
| Glycol Distearate, Steateth-4 | 2.0% |

Example Formulation 3.9

Shampoo

| | |
|---|---|
| Sodium Laureth Sulfate (28%) | 35% |
| Perfume | 0.5% |
| Water | ad 100% |
| Sphinganine | 0.2% |
| Quaternium-80 | 0.5% |
| PEG/PPG-4/12 Dimethicone | 0.5% |
| Cocamidopropyl Betaine | 11.0% |
| PEG-120 Methyl Glucose Dioleate | 0.9% |

Example Formulation 3.10

O/W Deodorant Cream

| | |
|---|---|
| Zinc Ricinoleate | 2.0% |
| Glyceryl Stearate | 4.0% |
| Isopropyl Myristate | 4.0% |
| Cetyl Alcohol | 2.7% |
| Ceteareth-12 | 2.0% |
| Polyglyceryl-3 Beeswax | 1.0% |
| Sphinganine | 0.1% |
| Glycerin | 3.0% |
| Water | 80.8% |
| Citric acid (50%) | 0.4% |

Example Formulation 3.11

Deodorant Spray

| | |
|---|---|
| Zinc Ricinoleate; Triethanolamine; Dipropylene Glycol; Lactic acid | 1.2% |
| Polyglyceryl-3 Caprylate | 0.4% |
| PEG-8 | 1.4% |
| Cyclomethicone | 1.4% |
| Alcohol denat. | 25.6% |
| Sphinganine | 0.1% |
| Propane/Butane | 69.9% |

Example Formulation 3.12

24 h Antiperspirant/Deodorant Stick

| | |
|---|---|
| PPG-11 Stearyl Ether | 5.0% |
| PPG-3 Myristyl Ether | 5.0% |
| Stearyl Alcohol | 16.25% |
| Hydrogenated Castor Oil | 1.75% |
| Sphinganine | 0.2% |
| Cyclopentasiloxane (and) Cyclohexasiloxane | 44.3% |
| Silica Dimethylsilylate | 3.0% |
| Aluminium Chlorohydrate | 20.0% |
| Polyglyceryl-3 Caprylate | 0.5% |
| Zinc Ricinoleate; Lysine; Propylene | 4.0% |

Example Formulation 3.13

Deodorant Roll-On

| | |
|---|---|
| Polyglyceryl-3 Caprylate | 0.5% |
| Laureth-23 | 3.0% |
| Sphinganine | 0.1% |
| Perfume | 0.5% |
| PEG-14 Dimethicone | 0.5% |
| Alcohol | 20% |
| PEG-7 Glyceryl Cocoate | 1.0% |
| Water | 16.7% |
| Allantoin | 0.2% |
| Panthenol | 0.1% |
| Aluminium Chlorohydrate, 50% Solution | 20.0% |
| Hydroxyethylcellulose | 0.75% |
| Water | 36.65% |
| Preservative | q.s. |

Example Formulation 3.14

Cleansing Toner

| | |
|---|---|
| Polyglyceryl-4 Caprate | 1.0% |
| Phytosphingosine Hydrochloride | 0.05% |
| Sphinganine | 0.05% |
| Ethanol | 10.0% |
| Perfume | 0.2% |
| Water | 87.6% |
| Sodium Lactate; Sodium PCA; Glycine; Fructose; Urea; niacinamide; Inositol; Sodium Benzoate; Lactic Acid | 1.0% |
| Panthenol | 0.1% |
| Preservative | q.s. |

Example Formulation 3.15

Cleansing Face Foam

| | |
|---|---|
| Disodium PEG-5 Laurylcitrate Sulfosuccinate; Sodium Laureth Sulfate | 8.0% |
| Sodium Cocoamphoacetate | 12.0% |
| Capryl/Capramidopropyl Betaine | 2.0% |
| Polyglyceryl-3 Caprate | 0.3% |
| PPG-3 Myristyl Ether | 0.5% |
| Sphinganine | 0.1% |
| Water | 77.2% |
| D-Panthenol | 0.2% |
| Creatine | 0.5% |
| Methoxy PEG/PPG-7/3 Aminopropyl Dimethicone | 0.2% |

Example Formulation 3.16

Conditioning Antidandruff Shampoo

| | |
|---|---|
| Glycol Distearate | 3.0% |
| Sodium Laureth Sulfate, 28% | 40.0% |
| Sphinganine | 0.05% |
| Perfume | 0.3% |
| Zinc Pyrithione, 48% | 2.0% |
| Quaternium-80 | 1.0% |
| Water | 36.65% |
| Acrylates/C10-30 Alkyl Acrylate Crosspolymer | 0.2% |
| Polyquaternium-10 | 0.3% |
| NaOH, 25% | 0.3% |
| Undecylenamidopropyl Betaine | 12.5% |
| Isostearamide MIPA | 3.5% |

Example Formulation 3.17

Shampoo

| | |
|---|---|
| Sodium Lauryl Sulfate, 28% | 50.0% |
| Sucrose Cocoate | 2.9% |
| Perfume | 0.5% |
| Quaternium-80 | 0.3% |
| Water | 34.45% |
| D-Panthenol | 1.5% |
| Cocamidopropyl Betaine | 6.4% |
| PEG-18 Glyceryl Oleate/Cocoate | 1.0% |
| Glycol Distearate; Stearth-4 | 2.5% |
| Sphinganine | 0.05% |
| Preservative | q.s. |
| NaCl | q.s. |

Example Formulation 3.18

Conditioning Hair Rinse

| | |
|---|---|
| Ceteareth-25 | 0.5% |
| Cetearyl Alcohol | 2.5% |
| Distearyldimonium Chloride | 1.0% |
| Isocetyl Alcohol; Ceramide NP; Cetyl Alcohol | 2.0% |
| Glyceryl Stearate | 1.5% |
| Sphinganine | 0.05% |
| Glycerin | 3.0% |
| Quaternium-80 | 1.0% |
| Water | 88.45% |
| Citric acid | ad pH = 4 |
| Preservative | q.s. |
| Perfume | q.s. |

Example Formulation 3.19

Dental Cream

| | |
|---|---|
| Dicalcium Phosphate | 47.5% |
| Glycerin, 86% | 30.0% |
| Flavour | 1.0% |
| Saccharin, 1% | 0.5% |
| Sodium Lauryl Sulfate | 1.0% |
| Sphinganine | 0.1% |
| Water | 19.9% |

Example Formulation 3.20

Anti-Caries Gel

| | |
|---|---|
| Glycerin | 10.0% |
| Sodium Metaphosphate | 30.0% |
| Titanium Dioxide | 1.0% |
| Silica | 3.0% |
| Cetylamine Hydrofluoride | 1.0% |
| Olaflur | 2.0% |
| Methylparaben | 0.15% |
| Mineral oil | 1.0% |
| Saccharin | 0.03% |
| Menthol | 0.2% |
| Flavour/Aroma | 1.0% |
| Cocamidopropyl Betaine | 3.0% |
| Sphinganine | 0.1% |
| Water | 47.52% |

The invention claimed is:

1. A method of treating a skin condition, said method comprising applying an effective amount of sphinganine to human skin, wherein said applying reduces the amount of sebum production of said human skin, and wherein said skin condition is oily skin.

2. The method of claim 1, wherein said skin sebum production is reduced about 17%.

3. The method of claim 1, wherein said sphinganine is a component of a cosmetic composition or a cosmetic formulation.

4. The method of claim 3, wherein said applying comprises a topical application of said cosmetic composition or said cosmetic formulation.

5. The method of claim 3, wherein said cosmetic composition or said cosmetic formulation is selected from the group consisting of a sunscreen lotion, an oil-in-water (O/W) lotion, a O/W cream, a water-in-oil (W/O) lotion, a massage oil, a shower gel, a cleansing toner, and a cleansing face foam.

6. The method of claim 1, wherein said applying comprises a leave-on or leave-in application of said sphinganine.

7. The method of claim 1, wherein said applying comprises a rinse-off application of said sphinganine.

8. The method of claim 1 wherein said effective amount of sphinganine is 0.1%.

* * * * *